United States Patent [19]

Asakawa et al.

[11] Patent Number: 5,324,823
[45] Date of Patent: Jun. 28, 1994

[54] ADSORBENT FOR CELLULAR FIBRONECTIN AND A METHOD FOR FRACTIONAL PURIFICATION OF FIBRONECTIN

[75] Inventors: Kaneji Asakawa, Tokushima; Ryoichi Umemoto, Naruto; Kazuo Hino, Tokushima; Eiji Sakashita, Itano; Takashi Komai, Sapporo, all of Japan

[73] Assignee: Otsuka Pharmaceutical Factory, Inc., Naruto, Japan

[21] Appl. No.: 946,370

[22] PCT Filed: Mar. 25, 1992

[86] PCT No.: PCT/JP92/00359
§ 371 Date: Nov. 19, 1992
§ 102(e) Date: Nov. 19, 1992

[87] PCT Pub. No.: WO92/17502
PCT Pub. Date: Oct. 15, 1992

[30] Foreign Application Priority Data

Mar. 26, 1991 [JP] Japan .................................. 3-61535

[51] Int. Cl.$^5$ .......................... C07K 3/00; C07K 15/00
[52] U.S. Cl. ...................................... 530/415; 536/20; 536/21; 536/33; 536/59; 536/61; 536/100; 530/395; 530/412; 530/413; 530/417; 530/425
[58] Field of Search ................................ 514/8, 54–59, 514/21; 536/20, 21, 33, 61, 59, 106; 435/7.92; 530/415, 395, 427, 417, 412, 413

[56] References Cited

U.S. PATENT DOCUMENTS 5,120,715  6/1992  Kato et al. .......................... 145/21

OTHER PUBLICATIONS

JPOABS Japan 59-102436 (Oct. 4, 1984 Rb. Date ABS) Tani et al "Adsorbent Body".
Siri et al., Eur. J. Biochem., vol. 154, No. 3, (1986), pp. 533–538.
Borsi et al., FEBS Lett., vol. 192, No. 1, (1985), pp. 71–74.
Sekiguchi et al., J. Biol. Chem., vol. 260, No. 8, (1985), pp. 5105–5114.

*Primary Examiner*—Herbert J. Lilling
*Attorney, Agent, or Firm*—Armstrong, Westerman, Hattori, McLeland & Naughton

[57] ABSTRACT

The invention provides a selective adsorbent for cellular fibronectin (cFN) and a method for fractional purification of FN which includes contacting an FN material containing plasma fibronectin (pFN) and cFN with a crosslinked polysaccharide sulfate and/or an immobilized polysaccharide sulfate to fractionate the pFN and cFN.

By the fractional purification method of the invention, cFN and pFN can be fractionated in an expedient manner and with high efficiency and both pFN and cFN can be recovered in high purity and good yield.

7 Claims, 2 Drawing Sheets

ADSORBENT FOR CELLULAR FIBRONECTIN AND A METHOD FOR FRACTIONAL PURIFICATION OF FIBRONECTIN

TECHNICAL FIELD

The present invention relates to a selective adsorbent for cellular fibronectin (cFN) and a technology for fractional purification of fibronectin (FN), particularly a method for fractionating an FN material containing both plasma fibronectin (pFN) and cFN into pFN and cFN and a method for eliminating cFN from blood by the first-mentioned method.

BACKGROUND ART

Fibronectin (FN) was first reported by Morrison et al. [Morrison, P. R. et al., J. Am. Chem. Soc., 70, 3103 (1948)] as one of plasma proteins in 1948. Being a multifunctional protein broadly distributed in various tissues and body fluids, this substance is known to be involved, as a cell adhesion factor, in a large variety of biological events such as the migration, differentiation, proliferation and canceration of cells [Sekiguchi, K.: Cell Engineering, 4 (6), 485–497 (1985)].

Meanwhile, FN as it is synthesized in the liver and occurring in the blood is known as plasma FN (pFN), and FN as it is detected on the cultured cell surface and culture medium is called cellular FN (cFN) [Sekiguchi et al., J. Biol. Chem., 260 (8) 5105–5114 (1985)]. It has been shown that these species of FN are subject to molecular diversity due to alternative splicing of the early gene transcription product. As the regions subject to such alternative splicing, there are three regions called EDA, EDB and IIIcs, and it is believed that a large number of molecular species occur according to varied combinations of expression of these regions. In pFN, the above-mentioned EDA and EDB regions have not been appreciably expressed. On the other hand, cFN is an FN with a high degree of expression of said EDA region. Peters J. H. et al. conjugated a peptide having 29 amino acids with keyhole limpet hemocyanin (KLH) to prepare an immunogen, constructed an anti-cFN polyclonal antibody specifically reactive to cFN having the EDA region, and using the antibody, demonstrated that the normal human blood contains traces of cFN and that the blood cFN level is markedly elevated in patients with collagen disease accompanied by vasculitis [Am. Rev. Respir. Dis., 138, 167–174 (1988); J. Lab. Clin. Med., 113 (5), 586–597 (1989)]. According to the above report of Peters et al., the physiological implications of increased blood cFN in patients with collagen disease accompanied by vasculitis are not definitely known but a correlation between the stage or severity of disease and the blood concentration of cFN is suggested. The investigation made by the inventors of the present invention using the anti-cFN monoclonal antibody which is to be described hereinafter revealed that whereas the plasma concentration of cFN in healthy humans is 1 to 2 $\mu$g/ml, it is 4 to 8 $\mu$g/ml in patients with various diseases and as high as 10 and odd $\mu$g/ml in seriously ill patients. On the other hand, pFN is invariably within the normal range of 270 to 400 $\mu$g/ml, irrespective of subjects.

Therefore, it is a subject of intriguing interest to investigate how the course of disease is modified by selective elimination of cFN from the blood of patients with collagen disease presenting with abnormal elevations of cFN. The recent study by the inventors of the present invention uncovered that when the plasma of a patient with rheumatoid arthritis is subjected to cryofiltration, cFN is partially removed from the plasma, resulting in relief of the symptoms. However, the cryofiltration procedure is disadvantageous in that it involves discarding of the useful plasma protein in large quantities and is not capable of selective elimination of cFN. Thus, both a technology for selective elimination of cFN from the patient's blood nor a selective adsorbent for such elimination remained to be developed. Furthermore, detailed research into the physiological role of cFN in patients with collagen disease and the functions and physiological implications of pFN and cFN require pFN and cFN in the pure form but since the difference between pFN and cFN, in structure, is of the minuscule order on a molecular scale, they cannot be successfully fractionated from each other by known purification procedures [Katayama, M., J. Medical Technology, 34, 1725 (1990)]. For example, gelatin affinity chromatography [Hynes, R. O. (ed): Fibronectins, p9–14, Springer-Verlag, 1990] has heretofore been employed for the purification of FN but since there is no difference in the affinity for gelatin between pFN and cFN, even this method is not able to fractionate them from each other. Furthermore, because the molecular weight differential between pFN and cFN is extremely small, the routine purification methods for proteins, such as gel permeation chromatography, are also ineffective in the fractionation of these substances.

As the result of their intensive research, the inventors of the present invention developed a monoclonal antibody which recognizes the amino acid sequence of the EDA region of FN and using this antibody, successfully established a high-precision cFN assay method. Further research with the aid of this assay method led to the discovery that sulfated polysaccharides, represented by heparin, have a specific affinity for cFN. The inventors further made explorations starting from the above discovery and found that a water-insoluble crosslinked polysaccharide sulfate obtainable by subjecting the corresponding sulfated polysaccharide to crosslinking reaction and an immobilized polysaccharide sulfate obtainable by immobilizing a sulfated polysaccharide as a ligand on a water-insoluble support or carrier exhibit dissimilar adsorbent affinities for cFN and pFN and, hence, is a useful selective adsorbent for cFN. Based on these facts, the inventors developed a new technology by which pFN and cFN can be successfully fractionated from each other. The present invention has been developed on the basis of the above technology.

DISCLOSURE OF INVENTION

The present invention is, therefore, directed to a cFN adsorbent consisting in a crosslinked polysaccharide sulfate and/or an immobilized polysaccharide sulfate and a method for fractional purification of FN characterized by contacting an FN material containing both pFN and cFN with said adsorbent to fractionally isolate pFN and cFN.

The FN material, which is the object of treatment according to the invention, may be any material that contains both pFN and cFN. Typically, it includes the blood, plasma, serum, extracts of various organs in which the existence of FN has been established, and FN fractions derived from fibroblast and other cultures. Preferred, among them, is the blood (plasma and serum) of patients with various diseases known to be accompanied by elevation of blood cFN, such as rheumatoid arthritis, systemic lupus erythematosis, progressive systemic sclerosis, polymyositis, giant cell arteritis, polymyalgia rheumatica, polyarteritis nodosa, chronic renal failure and so on.

The cFN adsorbent of the present invention consists in a crosslinked polysaccharide sulfate and/or an immobilized polysaccharide sulfate with a crosslinked polysaccharide and the fractional isolation method of the invention comprises contacting an FN-containing material with said adsorbent.

The crosslinked polysaccharide sulfate which can be utilized as the above-mentioned adsorbent in the practice of the invention includes sulfuric acid esters of crosslinked polysaccharides, such as those obtainable by crosslinking dextran, and various salts thereof, such as the corresponding sodium, potassium, ammonium, trimethylammonium and other salts, preferably sodium salts. These crosslinked polysaccharide sulfates are preferably water-insoluble and gel-like in the hydrated state. The starting polysaccharide includes cellulose, agarose, dextran, chitin and chitosan, to name a few typical examples. The above-mentioned cellulose includes, among others, polysaccharides each consisting of glucose units linked by $\beta$-1,4 glycosidic bonds and having a molecular weight in the range of about 50,000 to 2,000,000. Thus, crystalline cellulose derivatives such as Avicel (Asahi Chemical Industry) and Cellulofine (Chisso Corporation) can be mentioned as preferred examples. The above-mentioned agarose may be the polysaccharide which is a principal component of agar, namely a polysaccharide having the repeating [D-galactosyl-($\beta$-1,4)-3,6-anhydro-L-galactosyl-($\alpha$-1,3)] structure, preferably in the molecular weight range of about 10,000 to about 5,000,000. Thus, Sepharose 2B, Sepharose 4B, Sepharose 6B, etc. (all manufactured by Pharmacia) can be mentioned as specific examples. The above-mentioned dextran includes, among others, those D-glucose polymers in which $\alpha$-1,6 bonds predominate, which certain microorganisms such as *Leuconostoc mesenteroides* elaborate from sucrose. The preferred range for the average molecular weight of such polymers is about 1,000 to 40,000,000. As said chitin and chitosan, partially deacetylated chitin and partially deacetylated chitosan which are soluble in aqueous media such as dilute aqueous solutions of acetic acid, hydrochloric acid, etc. can be employed. These chitin and chitosan derivatives may be those which are readily available from commercial sources or those which can be obtained by subjecting a chitin isolated and purified from a crustacean among arthropods, such as the lobster, crab, etc., in the routine manner to heat treatment in an aqueous solution of alkali, e.g. sodium hydroxide or potassium hydroxide.

The crosslinking reaction of the above starting polysaccharide can be conducted using any of the known crosslinking agents such as epichlorohydrin, 2,3-dibromopropanol and so on. Furthermore, some crosslinked polysaccharides are also commercially available. As specific examples of such commercial products, there can be mentioned Sephadex G-10, Sephadex G-25, Sephadex G-50, Sephadex G-100, etc. (all are crosslinked dextrans) and Sepharose CL-2B, Sepharose CL-4B, Sepharose CL-6B (crosslinked agaroses), all of which are products of Pharmacia, and Cellulofine (crosslinked cellulose) which is manufactured by Chisso.

The sulfation reaction of said crosslinked polysaccharide can be carried out in the conventional manner using a variety of known sulfating agents such as chlorosulfonic acid, anhydrous sulfuric esters and so on. Sulfuric esters of the above-mentioned crosslinked polysaccharides are also available on the market and can be utilized as they are. Among such commercial products are Sulfated Cellulofine (crosslinked cellulose sulfate), Sulfated Sephadex (crosslinked dextran sulfate) and Sulfated Sepharose (crosslinked agarose sulfate), which are manufactured by Seikagaku Corporation, and Sulfonated Chitopearl (crosslinked chitin sulfate, crosslinked chitosan sulfate), which is manufactured by Fuji Spinning Co. Among such sulfated products, those with higher sulfate densities are preferred. Generally speaking, the higher the sulfate density, the larger is the amount of cFN adsorbed.

As the adsorbent according to the present invention, an immobilized polysaccharide sulfate can likewise be employed. The term 'immobilized polysaccharide sulfate' is used herein to denote a polysaccharide sulfate coupled to an appropriate solid support.

The polysaccharide sulfate includes, among others, heparin, dextran sulfate, chondroitin sulfate, chondroitin polysulfate, cellulose sulfate, chitin sulfate, chitosan sulfate, pectin sulfate, inulin sulfate, agarose sulfate and so on. Preferred are heparin, dextran sulfate and cellulose sulfate.

The solid support for immobilization of said polysaccharide sulfate may virtually be any solid support that is well known in the field of affinity chromatography. Generally speaking, it is preferably a water insoluble porous substance having open micropores which are large enough to permit entry of FN for efficient adsorption of FN from the material to be treated, such as plasma. It is preferable, too, that the support does not adsorb much of body fluid components other than the target FN (low nonspecific adsorption rate). Moreover, the support preferably carries on its surface those functional groups which can be utilized for the immobilization of the polysaccharide sulfate. Among such functional groups are hydroxyl, amino, aldehyde (inclusive of formyl), carboxyl, thiol, silanol, amide, epoxy, halogen, succinimide, acid anhydride and other groups. Particularly preferred are supports having amino and/or aldehyde (inclusive of formyl) groups. As specific examples of said water-insoluble porous substance, there may be mentioned the crosslinked polysaccharides mentioned hereinbefore, such as crosslinked cellulose, crosslinked dextran, crosslinked agarose, crosslinked chitin, etc., inorganic porous substances such as porous silica gel etc., synthetic polymers such as polyacrylamide, polymethyl methacrylate, polyvinyl alcohol, styrene-divinylbenzene copolymer, etc., and the corresponding porous polymer alloys or hard gels. As species of said water-insoluble porous support carrying functional groups such as amino, formyl etc., there can be mentioned Amino-Cellulofine (Chisso), Formyl-Cellulofine (ditto) and other crosslinked cellulose derivatives.

The coupling (immobilization) of said polysaccharide sulfate to such a solid support for the manufacture of the immobilized polysaccharide sulfate according to the invention can be carried out by an appropriate method which can be selected, according to the kind of support used, from among the various methods heretofore employed for immobilization of enzymes [cf. Chihata, Tosa & Matsuo, Experimental and Applied Affinity Chromatography and Affinity Labeling, Kyoritsu Publishing Co., 1980], e.g. by direct coupling through functional groups available on the support or, in the absence of functional groups, indirectly with the aid of an appropriate coupling agent.

The immobilization method is now described in detail, taking heparin as an example of polysaccharide sulfate.

When an amino-containing support is employed, the amino group can be directly reacted with the reducing-end aldehyde group or carboxyl group of heparin. In the case of a support having an aldehyde or epoxy group, the group can be coupled to the primary amino group of heparin. When it is suspected that insufficient binding will be obtained with the primary amino group of heparin alone, some of the —NHSO$_3$— groups of heparin may be converted to primary amino groups by desulfation and, then, subjected to the above coupling reaction. When a support not having suitable functional groups is utilized, the desired heparin can be obtained by reacting the support with a coupling agent having a suitable functional group and reacting the reaction product with heparin. The reaction for introducing a functional group into the support through the use of a coupling agent can be carried out by any of the known processes such as the CNBr process, epoxy activation method, formylation method and so on. The CNBr process represents the most popular technique and comprises activating a polysaccharide support with CNBr under alkaline conditions from pH 11 to pH 12. By this process, heparin containing amino groups can be easily coupled in carbonate or borate buffer at pH about 9. By this technology, a spacer group can also be introduced using an $\omega$-aminoalkylamine [NH$_2$(CH$_2$)$_n$NH$_2$]. In the epoxy activation method, the spacer and epoxy groups are introduced into a polysaccharide support using 1,4-butanediol glycidyl ether, epichlorohydrin or the like. To the resulting support can heparin be coupled with ease. The formylation method comprises treating the support with epichlorohydrin or the like, then treating it with aqueous ammonia to effect cleavage of epoxy groups and introduction of amino groups and, then, introducing formyl groups. To this support can heparin containing amino groups be coupled with ease in the presence of a reducing agent such as dimethylamine.

In any of the above processes, the amount of heparin to be coupled to the support is not limiting but the larger the amount of heparin coupled, the higher is the FN fractionating efficiency of the resulting adsorbent; in other words, such an adsorbent is desirable for purposes of the present invention. Some such activated supports for immobilization of heparin are commercially available, and include, among others, CNBr-activated Sepharose 4B (Pharmacia), which is an imidocarbonated agarose, Affigel 10 and 15 (Bio-Rad), which are N-hydroxysuccinimide-activated agaroses, activated CH-Sepharose 4B (Pharmacia), AF-Epoxy-Toyopearl (Tosoh Corporation), which is an epoxy-activated hydrophilic polymer, Epoxy-activated Sepharose 6B (Pharmacia), which is an epoxy-activated agarose, Formyl-Cellulofine (Chisso), which is a formylated cellulose, AF-Formyl-Toyopearl (Tosoh), which is a formylated hydrophilic polymer, and so on.

The immobilization of sulfated polysaccharides other than heparin can be carried out in substantially the same manner. Aside from the above methods, the conventional epichlorohydrin method, the method using a polyoxirane compound such as bisepoxide, the triazine halide method, etc. can likewise be selectively employed.

Thus can be obtained the immobilized polysaccharide sulfate as the cFN adsorbent of the invention.

The method of the present invention is now described in deail. The method comprises contacting an adsorbent consisting in said crosslinked polysaccharide sulfate and/or said immobilized polysaccharide sulfate with an FN-containing material. This contacting step can be carried out by whichever of the batch method which comprises contacting them in one and the same system and the column method which comprises passing the FN-containing material through a column packed with said crosslinked polysaccharide sulfate and/or immobilized polysaccharide sulfate, although the column method is generally preferred because of its greater convenience. This column treatment can be carried out in the same manner as the conventional affinity column chromatography. Specifically, an appropriate column is packed with the crosslinked polysaccharide sulfate and/or immobilized polysaccharide sulfate in the gel form and, then, washed thoroughly with a suitable buffer such as 20 mM phosphate buffer (pH 7.0) for equilibration. Then, the FN-containing material is applied on the column. The amount of the gel is not limiting but can be selected according to the species of gel used and of the FN-containing material. Generally, however, the amount of the gel can be appropriately selected from the range of about 1 to 200 ml per mg of cFN in the FN-containing material. The loading velocity for the FN-containing material is dependent on the geometry of the used column but can be generally selected from the range of about 10 to 300 ml/hr·cm$^2$. After the FN-containing material has been loaded on the column in the above manner, the column is thoroughly washed and the FN adsorbed on the gel in the column is eluted and recovered with a buffer solution with increasing ionic strength in the conventional manner. As a method for increasing the ionic strength of the buffer, there may be mentioned the method comprising adding a salt such as NaCl or the method employing a buffer of increasing concentration. Elution, in the column method, can be carried out by the gradient method. Thus, continuous elution and recovery can be carried out, for instance, as the concentration of NaCl, in the elution buffer is gradually increased from about 0 to about 2.0M. In such gradient elution, pFN is eluted in low NaCl concentration fractions and cFN is then eluted in high NaCl fractions. Thus, in accordance with the method of the invention, pFN and cFN can be respectively recovered in extremely high purity and good yield.

In the embodiment of the invention wherein an immobilized heparin is used as the adsorbent, generally the above-mentioned column treatment is preferably carried out at a temperature within the range of about 10° to 40° C., whereby the selective adsorption of cFN is accomplished. If the treating temperature is too much below 10° C., the inherent selective adsorption capacity of this adsorbent tends to be adversely affected.

In the above column method, by selecting an appropriate ionic strength beforehand, it can be insured so that, on loading of the FN-containing material, only pFN is allowed to pass through the column as the effluent while only cFN is adsorbed on the gel. In this arrangement, pFN in isolation from cFN can be obtained directly from the FN-containing material.

Thus, in accordance with the present invention, cFN and pFN can be fractionally purified from an FN-containing material with the utmost expediency and, also, pFN of high purity not contaminated with cFN can be successfully isolated.

Particularly by applying the method of the present invention to the manufacture of a blood preparation, a plasma protein fractional preparation or the like, it can be insured that the preparation will be completely free of cFN. Purification of the blood preparation or the like can be carried out fundamentally in the same manner as above. More particularly, when a plasma protein fraction is to be purified with a heparin-bound crosslinked cellulose gel, for instance, a cFN-free plasma protein fraction can be obtained by mixing the plasma with about 1/20 to 1/5 volume, preferably about 1/15 to 1/10 volume, of the heparin-bound cellulose gel and, after stirring, centrifuging the gel. The above removal of cFN can be carried out also by the column method and in any optional stage in the manufacture of a protein fraction. The adsorbent gel used in the above method can be easily regenerated by washing it with an appropriate regenerating solution such as 2–5M NaCl solution or 6M urea solution.

While the present invention provides the above method for separation of pFN and cFN from an FN-containing material and for selective isolation of pFN, cFN in the systemic circulation can be removed by applying the method to an extracorporeal circulation system. This application is now described in detail. It should be understood that, in the following description, removal of an excess of cFN over the nominal range from the blood will hereinafter referred to briefly as "blood cleansing".

The extracorporeal shunt or circuit may be of any optional type except that it is provided with an appropriate device for contacting the blood or the plasma or other component of blood with the adsorbent of the invention. The device mentioned above may for example be a plasma component adsorption module. The module preferably comprises (1) an appropriate container, which may be made of a material inert to the substances occurring in blood, such as polycarbonate, polypropylene or other resin, and is equipped with an inlet for admission of the blood to be treated and an outlet for returning the treated blood, preferably a cylindrical container with an appropriate diameter-to-length ratio, (2) an adsorbent gel according to the invention as packed into said container and (3) a filter with an appropriate pore size, through which the blood may pass freely but the gel cannot, as disposed at either open end of said container. Though there is no limitation on the capacity of said container, a container capable of holding about 50 to 500 ml of said gel can be employed. By building this module, in lieu of the plasma separator or plasma component separator, into the existing double filtration plasma exchanger having an extracorporeal circuit, an extracorporeal blood cleansing system can be constructed. Of course, when the above module is used in lieu of the plasma separator for blood cleansing, the circuit and hardware relevant to the plasma separator are not required, and when the module is used in lieu of the plasma component separator, the circuit and operation for replacement fluid are not required.

By the method for fractional purification of FN according to the invention, only cFN can be effectively removed from the blood and this is a real breakthrough in that by applying the method to patients with collagen disease accompanied by vasculitis and presenting with increased blood cFN titers, such as those with rheumatoid arthritis, systemic lupus erythematosis, progressive systemic sclerosis, polymyositis, giant cell arteritis, polymyalgia rheumatica, polyarteritis nodosa, chronic renal failure or the like, symptomatic improvements can be obtained in such patients.

BEST MODE FOR CARRYING OUT THE INVENTION

The following reference, working and application examples are intended to illustrate the present invention in further detail.

Reference Example 1 is a production example for the monoclonal antibody (HHS-01 antibody) specifically reactive to cFN, which was utilized in the assay of cFN for verifying the fractionation of cFN and pFN by the method of the invention, and Reference Example 2 pertains to the method for assay of cFN employing the above antibody.

Example 1, Example 2 and Examples 4 through 9 are examples of preparation of the crosslinked polysaccharide sulfate and immobilized polysaccharide sulfate for use in the method for fractional purification of FN in accordance with the present invention and Example 3 and Examples 10 through 12 are examples of working the method of the invention. Lastly, a method for cleansing the blood in an extracorporeal circulation system applying the method of the invention is described as an application example.

It should be noted that in the respective examples, the total FN, albumin and total protein were determined by the following methods.

Determination of total FN

An anti-FN monoclonal antibody [OAL-pF117, established using Sigma pFN as the immunogen; cf. Japanese Journal of Clinical Pathology, Vol. 35 Supplement, p. 119 (1987); The 18th Congress of International Association of Medical Laboratory Technologists, Abstracts, p. 225 (1988); etc.] was dissolved in Dulbecco's phosphate buffer (pH 7.2; hereinafter referred to briefly as D'PBS) at a final concentration of 2 $\mu$g/ml and the solution was distributed, 100 $\mu$l/well, into the wells of a 96-well plastic microtiter plate and allowed to stand at 4° C. overnight for conversion to a solid phase, which was then washed once with D'PBS [containing 0.05% of Tween 20; 300 $\mu$l/well]. Thereafter, each well was filled with 300 $\mu$l each of D'PBS, 0.05% thimerosal and 0.5% bovine serum albumin (BSA) and allowed to stand at 4° C. overnight for blocking. After blocking, the plate was washed once with D'PBS [containing 0.05% of Tween 20; 300 $\mu$l/well] and each well was filled with 100 $\mu$l of D'PBS [containing 0.05% thimerosal, 10 mM EDTA, 0.1% BSA and 0.1% CHAPS] (buffer B). Furthermore, each well was filled with 20 $\mu$l each of the sample diluted 200-fold with buffer B and, as standard solutions, FN purified from nominal human plasma and diluted to varying concentrations, and the plate was incubated at room temperature for 2.5 hours. The microtiter plate was then washed 5 times with D'PBS containing 0.05% of Tween 20. Each well was further filled with 100 $\mu$l/well of the anti-FN monoclonal antibody [OAL-pF115, established by using Sigma pFN as the immunogen; Japanese Journal of Clinical Pathology, Vol. 35 Supplement, p. 119 (1987); The 18th Congress of International Association of Medical Laboratory Technologists, Abstracts, p. 225 (1988); etc.] coupled to peroxidase by the periodate method (a 5000-fold dilution, 100 μl/well; buffer, the remainder of buffer B after elimination of EDTA, 100 μl/well) and the plate was incubated for 2.5 hours and, then, washed 5 times with D'PBS containing 0.05% of Tween 20.

Then, 100 μl/well of o-phenylenediamine solution (OPD solution) was added and the reaction was carried out at room temperature for 10 minutes, at the end of which time the reaction was stopped with 100 μl of 2N sulfuric acid and the absorbance at 492 nm was measured. A calibration curve was constructed from the concentrations and absorbance values of standard FN solutions and the concentration of FN in the sample was determined from the calibration curve and the absorbance of the sample.

Determination of albumin

The assay of albumin was made by the BCG method using a Hitachi 705 automatic analyzer (Hitachi, Ltd.) [reagent: ALB reagent art. no. 7022 (Kokusai Shiyaku), standard solution: Monitorol I (Baxter Healthcare Corporation, control serum)].

Determination of total protein

The total protein was determined by the biuret method using a Hitachi 705 automatic analyzer (Hitachi, Ltd. [reagent: TP reagent art. no. 7677 (Kokusai Shiyaku), standard solution: Monitorol I (Baxter Healthcare Corporation, control serum).

REFERENCE EXAMPLE 1

Production of the monoclonal antibody (HHS-01) (1) Preparation of an EcoRI-SacI cDNA fragment including the EDA region of FN a) Amplification of the human fibroblast cDNA library Using the cDNA library (Clonetek) prepared from the poly A+ RNA of human fibroblast cell line IMR-90 using lambda phage λgtll as the vector, amplification of the phage was carried out by the plate lyric growth method. Thus, 1 μl of a phage suspension from the above cDNA library was diluted with 99 μl of SM medium [1M NaCl, 20 mM MgSO$_4$·7H$_2$O, 50 mM Tris-HCl and 0.1% gelatin] and mixed with 100 μl of an overnight culture of E. coli LE392 in LB medium [1% Bacto trypton, 0.5% Bacto yeast extract and 0.5% sodium chloride] and the mixture was incubated at 37° C. for 10 minutes, whereby the phage was adsorbed on the E. coli. To this was added 7.5 ml of a top agar solution [0.7% Bacto agar in LB medium] kept warm at about 50° C. and the mixture was overlayered on LB agar [LB medium containing 1.5% of Bacto agar] in a Petri dish 15 cm in diameter. After solidification of the top agar, culture was carried out at 37° C. overnight for phage amplification. Then, 15 ml of SM medium was poured on the top agar and the culture was incubated at 4° C. for 1 hour. The phage was recovered together with the top agar and centrifuged at 18000 rpm (Hitachi refrigerated centrifuge, RPR 20-2 rotors) for 10 minutes to remove the top agar and E. coli. To the phage-containing supernatant were added NaCl and polyethylene glycol at the final concentrations of 1M and 10%, respectively, and the mixture was allowed to stand on ice for 1 hour. The mixture was centrifuged again at 18000 rpm for 10 minutes to recover the phage as a pellet. This pellet was dissolved in 2 ml of 20 mM Tris-HCl (pH 7.5)-10 mM MgSO$_4$·7H$_2$O followed by addition of 20 μl of DNase I (10 mg/ml). The mixture was allowed to stand at room temperature for 30 minutes to lyze the free DNA and the same volume of chloroform was added and stirred for 5 minutes and centrifuged at 3000 rpm for 10 minutes to separate the water layer from the chloroform layer. The water layer was recovered and stirred well with the same volume of phenol to remove the coat protein from the phage particles, after which it was centrifuged at 3000 rpm for 10 minutes to transfer the phage DNA to the water layer. The water layer was extracted with the same volume of chloroform again and 0.2 volume of 3M sodium acetate solution and 2 volumes of ethanol were added to the water layer. The mixture was allowed to stand at −80° C. for 10 minutes and, then, centrifuged at 15000 rpm for 10 minutes to recover the phage DNA as a pellet. The DNA thus obtained was dissolved in TE buffer [10 mM Tris-HCl (pH 7.4)-1 mM EDTA] at a final concentration of 0.5 μg/μl and preserved at −20° C. The purity of phage DNA was verified by 1% agarose gel electrophoresis.

b) Synthesis of primers

The following two oligodeoxynucleotide primers were prepared.

Upstream primer (EcoRI site)

5'-TCTCGGAATTCCATCACCCTCACC-3'

Downstream primer (SacI site)

5'-GGGGAGCTCCGAGCATTGTCATTC-3'

The above primers were synthesized from β-cyanoethylphosphoamidite derivatives of 4 different bases by the solid-phase method using an automatic DNA synthesizer (Applied Biosystems 380A). The deprotection and detachment from the solid phase of the synthesized oligodeoxynucleotide were carried out by warming in the concentrated aqueous ammonia at 55° C. for 10 hours. The synthetic oligonucleotides thus prepared were purified by HPLC to give about 50 μg each of the desired oligonucleotides for use as the upstream and downstream primers. The resulting purified oligonucleotides were dissolved in TE buffer and preserved at −20° C.

c) Amplification of the EcoRI-SacI cDNA fragment

A 1 μl portion of the TE buffer containing 0.5 μg of DNA as prepared in a) above was diluted with 1×PCR reaction buffer [20 mM Tris-HCl, pH 8.4; 50 mM KCl; 2.5 mM MgCl$_2$; 0.1 mg/ml nuclease-free bovine serum albumin] containing 20 pmol each of the upstream and downstream primers, followed by addition of 5 U of Taq polymerase (Perkin Elmer-Cetus, 1 μl). After 100 μl of mineral oil was overlayered, the mixture was subjected to 30 heating cycles of 1.5 minutes at 95° C., 3 minutes at 50° C. and a further 3 minutes at 72° C. to amplify the EcoRI-SacI cDNA fragment coding for the desired EDA region. The above reaction mixture was subjected to 1% agarose gel electrophoresis using the HaeIII-cut DNA fragments of φ×174 DNA as molecular weight markers in the presence of ethidium bromide to confirm that the EcoRI-SacI cDNA fragment having the size of 1400 base pairs had been amplified.

d) Purification of the EcoRI-SacI cDNA fragment

The EcoRI-SacI fragment isolated on the agarose gel in c) above was adsorbed on a DEAE-cellulose membrane (S & S, NA 45) by the method of Dretzen, G. M. et al., [Anal. Biochem., 112, 295–298 (1981)] and the adsorbed DNA fragment was then eluted from the DEAE-cellulose membrane with an eluent buffer [50 mM Tris-HCl, pH 8.0; 1M NaCl; 10 mM EDTA] and precipitated with cold ethanol to recover the EcoRI-SacI fragment (about 100 ng).

(2) Insertion of the EcoRI-SacI cDNA including the EDA region into the protein A expression vector pRIT2T a) Preparation of the plasmid vector Two μg of protein A gene-fused vector pRIT2T (Pharmacia) was dissolved in 20 μl of EcoRI-SmaI reaction buffer [33 mM Tris-acetate, pH 7.9; 10 mM magnesium acetate; 66 mM potassium acetate; 0.5 mM dithiothreitol; 0.01% bovine serum albumin] followed by addition of 10 units each of EcoRI and SmaI. The mixture was incubated at 37° C. for 2 hours to cleave the plasmid DNA at EcoRI-SmaI sites. The reaction mixture was extracted with phenol and the cleaved DNA (about 1 μg) was recovered by ethanol precipitation.

b) Insertion of the PCR-amplified EcoRI-SacI cDNA fragment into the plasmid vector In 20 μl of EcoRI reaction buffer [50 mM Tris-HCl, pH7.5; 10 mM MgCl$_2$; 1 mM dithiothreitol; 100 mM NaCl] was dissolved 100 ng of the EcoRI-SacI cDNA fragment purified in (1)-d) above, followed by addition of 5 U of EcoRI, and the mixture was incubated at 37° C. for 3 hours to expose the 5' end EcoRI site of the amplified EcoRI-SacI fragment. The reaction mixture was then extracted with phenol and after addition of 20 ng of the pRIT2T plasmid cleaved at the EcoRI-SmaI site which was prepared in (2)-a), cold ethanol precipitation was carried out to recover the DNA. This DNA was dissolved in 24 μl of ligation buffer [66 mM Tris-HCl, pH 7.6; 5 mM MgCl$_2$; 5 mM dithiothreitol; 1 mM ATP] followed by addition of 300 U of T4 DNA ligase (Takara Shuzo), and the mixture was incubated at 16° C. for 16 hours to insert the EcoRI-SacI cDNA fragment encoding the EDA region of FN in the EcoRI-SmaI site of pRIT2T.

c) Preparation of the transformant

A 1 μl portion of the reaction mixture obtained in b) above was mixed with 100 μl of E. coli HB101 competent cells (Takara Shuzo) and the mixture was maintained under ice-cooling for 30 minutes and incubated at 42° C. for 90 seconds to introduce the plasmid DNA into the E. coli.

To this mixture was added 1 ml of LB medium and shake culture was carried out at 37° C. for 1 hour. Then, 100 μl of the culture was inoculated on LB agar medium containing 50 μg/ml of ampicillin and the inoculated agar was incubated at 37° C. for 14 hours to obtain about 50 colonies of E. coli transformed by the plasmid DNA. From among them, 12 colonies were randomly harvested and cultured in LB medium containing 50 μg/ml of ampicillin. Then, in accordance with the method of Birnboim and Doly as modified [Molecular Cloning, A Laboratory Manual, T. Maniatis et al., edit., 368-369 (1982)], the plasmid DNA was recovered from each colony. This DNA was double-digested with EcoRI and BamHI and a plasmid clone (pEDAl) having the predicted insert sequence of about 1400 base pairs was selected.

(3) Expression and isolation of the protein A-EDA fused protein a) Introduction of plasmid pEDA1 into E. coli N4830

The pEDA1 plasmid DNA obtained in (2) above was introduced into E. coli N4830 (obtained from Pharmacia) in accordance with the calcium phosphate method of Mandel and Higa [J. Mol. Biol., 53, 154 (1970)], as follows.

E. coli N4830 was shake-cultured in 100 ml of LB medium at 37° C. and when the cell density reached about $5 \times 10^7$/ml, the incubation was terminated and the culture was quenched in an ice bath. The quenched culture was centrifuged at 4000×g (4° C.) for 5 minutes to harvest the cells. The pellet was suspended in 50 ml of ice-cooled 50 mM calcium chloride-10 mM Tris-HCl (pH 8.0) and the suspension was allowed to stand in an ice bath for 15 minutes and, then, centrifuged at 4000×g (4° C.) for 5 minutes. The resulting pellet was resuspended in 7 ml of an ice-cooled solution of 50 mM calcium chloride-10 mM Tris-HCl (pH 8.0) and the suspension was allowed to stand in an ice bath. To 0.2 ml of the E. coli cell suspension thus prepared was added 10 μl of a solution of pEDA1 plasmid in TE buffer (containing 10 ng of plasmid DNA) and the mixture was allowed to stand in an ice bath for 30 minutes, after which it was warmed in a water bath at 42° C. for 2 minutes. After 1 ml of LB medium was added, the mixture was incubated at 37° C. for 1 hour. The E. coli cell suspension thus obtained, 100 μl, was spread on an ampicillin-containing LB agar medium and incubated at 37° C. for 14 hours to cause production of transformant E. coli colonies.

b) Isolation of the protein A-EDA fused protein

The transformant obtained in a) above (E. coli N4830 transformed with pEDA 1 plasmid) was shake-cultured in 500 ml of LB medium at 30° C. for 14 hours, and after 500 ml of LB medium warmed to 54° C. beforehand was added, shake culture was further continued in a water bath at 42° C. for 90 minutes to induce expression of the protein A-EDA fused protein.

The culture was centrifuged at 5000×g (4° C.) for 15 minutes to recover the cells, which were then suspended in 100 ml of ice-cooled Tris-buffered physiological saline [50 mM Tris-HCl (pH 7.6), and 150 mM NaCl] and disrupted by sonication in an ice bath (Branson Sonifier 250; 3 cycles of 3-minute treatment at output setting 7) to thereby release the protein from the cells. About 100 ml of this fluid was centrifuged (16000×g, 20 minutes, 4° C.) to recover about 95 ml of a supernatant fraction. This fraction was diluted with 300 ml of Tris-buffered physiological saline and applied to a column packed with about 10 ml of IgG-Sepharose 6 Fast Flow (Pharmacia) for adsorption of the protein A-EDA fused protein. This column was washed with 100 ml of Tris-buffered physiological saline and 20 ml of 5 mM ammonium acetate (pH 5.0) in that order and the adsorbed protein was eluted with 0.5M acetic acid solution. The protein A-EDA fused protein was dialyzed against Tris-buffered physiological saline for 48 hours to give about 1 mg of the target antigen.

(4) Preparation of the hybridoma

The purified protein A-EDA fused protein obtained in (3) above, 0.05 mg, was diluted with 0.5 ml of PBS and emulsified with the same quantity of complete Freund's adjuvant. The resulting emulsion was administered intradermally in 0.2 ml portions to male Balb/c mice (aged 8 weeks). The mice were immunized by further 4 similar doses given at 2-week intervals and the spleen was excised 3 days after the last immunization.

Splenic cells were isolated from the excised spleen and the erythrocytes present among the cells were removed by 1-2 minute lysis with 0.83% ammonium chloride solution at 4° C. The cells thus obtained were collected as sensitized lymphocytes and washed three times with RPMI-1640 medium prewarmed to 37° C.

Then, mouse myeloma cells [P3U1, Current Topics in Microbiology and Immunology, 73, 3 (1981)] was subcultured in a medium prepared by adding 100 $\mu$M of 8-azaguanine to RPMI-1640 supplemented with 15% FCS (fetal calf serum) and the cultured cells, designated as myeloma cells, were washed.

The above sensitized lymphocytes were mixed with the myeloma cells in a cell count ratio of 10:1 in a 50 ml tube and the resulting cell mixture was centrifuged at 500$\times$g for 5 minutes. The supernatant was thoroughly removed with a Pasteur's pipet. The above procedure was carried out in a water bath maintained at 37° C.

Then, 4 ml of 35% polyethylene glycol 1500 (Wako Pure Chemical; PEG) was added and the mixture was stirred gently for 1 to 2 minutes and allowed to stand for 1 minute, at the end of which time 2 ml of FCS-free RPMI-1640 medium, prewarmed to 37° C., was gradually added over a period of about 1 minute. The mixture was allowed to stand for 1 minute and 4 ml of the same medium was further added. After further 2-minute standing, 4 ml of the same medium was further added and the mixture was allowed to stand for 4 minutes. Thereafter, 8 ml of RPMI-1640 containing 15% FCS, 0.05 U/l of streptomycin sulfate, 60000 U/l of potassium penicillin G, 54 mg/l of gentamicin and 1 ml of sodium piruvate (hereinafter referred to as complete RPMI-1640 medium), warmed to 37° C. beforehand, was added over a period of 2 to 3 minutes. The mixture was then centrifuged at 500$\times$g for 5 minutes. The supernatant was aspirated off and the splenocytes were suspended in complete RPMI-1640 medium, prewarmed to 37° C., at a concentration of $1\times10^6$ myeloma cells/ml. This suspension was then distributed, 0.1 ml per well, into the wells of a 96-well microtiter plate (Costar) and cultured in an incubator controlled at 37° C., 5% $CO_2$ and 100% RH for 24 hours. Thereafter, each well was filled with 0.1 ml of 10% FCS-added complete RPMI-1640 medium containing $1\times10^{-4}$M hypoxanthine, $4\times10^{-7}$M aminopterin and $1.6\times10^{-5}$M Thymidine (hereinafter referred to as HAT medium). On the 2nd and 3rd days, 0.1 ml each of the supernatant was aspirated and 0.1 ml each of fresh HAT medium was added instead. This change of medium was further performed every 2 to 3 days. On the 6th day, the supernatant was similarly aspirated and complete RPMI-1640 medium containing $1\times10^{-4}$M hypoxanthine and $1.6\times10^{-5}$M thymidine (hereinafter referred to as HT medium) was substituted. Thereafter, growth was maintained in complete RPMI-1640 medium.

After the cell fusion by the above procedure, colonies became grossly visible in 10 to 14-days. Starting when the cells had occupied one-quarter of the bottom surface area of the 96-well plate, the culture supernatant was tested by the enzyme-linked immunosorbent assay (ELISA) using an EDA-carrying human placental FN as the antigen and from the positive well, hybridoma cloning was immediately performed by the limiting dilution method [Methods in Enzymology 73, 3 (1981)]. Thus, using 20 ml of a 10% FCS-added RPMI-1640 medium prepared to contain $1\times10^8$ Balb/c mouse thymic cells, cloning was performed by seeding a 96-well microtiter plate with 0.2 ml portions of the hybridoma at the rates of 3 cells/well, 1 cell/well and 0.3 cell/well to establish the terget hybridoma.

The above cloning was performed 4 times with monitoring to confirm lack of reactivity with plasma FN using, as an indicator, the reactivity with the placental FN and cellular FN purified from a cultured supernatant of the WI-38VA13 cell line which had been established by infecting the human normal fibroblast cell line WI-38 with the tumor virus SV40. By the above procedure was obtained a hybridoma producing the monoclonal antibody with the desired reaction selectivity. This hybridoma clone was designated as HHS-01.

The clone HHS-01 obtained above was cultured in complete RPMI-1640 medium under the conditions of 5% $CO_2$ and 37° C. for 96 hours. The resulting culture was centrifuged at 3,000 rpm for 10 minutes to obtain a culture supernatant containing the terget monoclonal antibody.

The thus-selected clone (hybridoma HHS-01 producing the antibody) has been deposited with the Fermentation Research Institute of the Agency of Industrial Science and Technology under the designation of HHS-01, where the accession number assigned is FERM BP-3297.

The above clone HHS-01 was intraperitoneally administered in a dose of $1\times10^6$ to Balb/c mice which had been inoculated with pristane (Aldrich). After 10 to 14 days, the accumulated ascitic fluid was harvested to recover an ascitic fluid containing the antibody.

The antibody in the ascites was purified by affinity chromatography using protein A-Sepharose to give a purified HHS-01 antibody.

The subclass of this antibody as determined by the Ouchterlony method using a monoclonal antibody typing kit (The Binding Site, code RK008) was $IgG_{2a}$.

REFERENCE EXAMPLE 2

Method for assay of cFN

The purified HHS-01 antibody obtained in Reference Example 1 was dissolved in D'PBS (pH 7.2) at a concentration of 2 $\mu$g/ml and this solution was distributed into the wells of a 96-well plastic microtiter plate in portions of 100 $\mu$l/well and allowed to stand at 4° C. overnight for adsorption onto plastic plate. The plate was then washed with D'PBS [containing 0.05% of Tween 20, 300 $\mu$l/well, once]. Then, each well was filled with 300 $\mu$l each of D'PBS, 0.05% thimerosal and 0.5% BSA and allowed to stand at 4° C. overnight for blocking. After blocking, the wells were washed with D'PBS [containing 0.05% of Tween 20, 300 $\mu$l/well, once] and each well was filled with 100 $\mu$l of 0.1M phosphate buffer [0.05% thimerosal, 10 mM EDTA, 20% normal goat serum and 1% normal mouse serum, pH 6.0] (buffer A). Then, each well was filled with 20 $\mu$l each of the sample solution and, as a standard solution, the cFN purified from a cultured supernatant of the cell line WI-38VA13, which had been obtained by infecting the human normal fibroblast cell line WI-38 with a tumor virus, and diluted at a varying concentration were added and the mixture was incubated at room temperature for 2.5 hours. The wells were, then, washed 5 times with D'PBS containing 0.05% of Tween 20. Then, each of the above wells was filled with 100 μl of the anti-FN monoclonal antibody [OAL-pF115] (5,000-fold dilution, 100 μl/well; buffer, the remainder of buffer A after elimination of EDTA) coupled to peroxidase by the periodate method and the mixture was incubated for 2.5 hours and washed 5 times with D'PBS containing 0.05% of Tween 20.

Then, 100 μl/well of OPD solution was added and the reaction was conducted at room temperature for 10 minutes. The reaction was terminated with 100 μl of 2N sulfuric acid and the absorbance at 492 nm was measured. A calibration curve was constructed from the concentrations and absorbance values of standard FN dilutions and the concentration of FN in the sample was determined from the calibration curve and the absorbance reading of the sample.

EXAMPLE 1

Preparation of an immobilized heparin

(1) Preparation of gel A

Amino-Cellulofine (Chisso), an amino-activated crosslinked cellulose gel, was washed with 10 volumes of distilled water. This procedure was repeated 3 times to recover a gel for use in the following procedure.

In 75 ml of 0.2M phosphate buffer (pH 7.0)-0.1 M NaCl was dissolved 2.0 g of heparin followed by addition of 50 ml of the above gel and 0.2 g of $NaCNBH_3$, and the mixture was shaken at 60° C. for 2 days. The gel was, then, recovered by filtration and washed thoroughly with distilled water to give an immobilized heparin. This gel was designated as gel A.

The concentrations of heparin in the supernatants before and after the above reaction were determined in terms of the concentration of sulfur in accordance with the Oxygen Flask Combustion Method of the Japanese Pharmacopoeia XI and the amount of concentration decrease was regarded as the amount of bound heparin. The amount of heparin coupled to gel A was 9.6 mg/ml gel. On the other hand, the concentrations of sulfur in the gel before and after the immobilization of heparin by the above method were measured and the amount of increase was regarded as the amount of bound heparin. As a result, the amount of heparin coupled to gel A was 4.3 mg/ml gel.

(2) Preparation of gel B

Using 1.0 g of heparin, the above procedure of (1) was otherwise repeated to give an immobilized heparin. This product was designated as gel B. The amount of coupled heparin, as measured in the supernatant, was 4.3 mg/ml gel and, as measured in the gel before and after immobilization of heparin, was 2.6 mg/ml gel.

(3) Preparation of gel C

Formyl-Cellulofine (Chisso), a formylated crosslinked cellulose gel, was washed with 10 volumes of distilled water. This procedure was repeated 3 times to recover a gel for use in the following procedure.

In 75 ml of 0.2M Na-K phosphate buffer (pH 7.0)-0.1M NaCl was dissolved 1.0 g of heparin followed by addition of 50 ml of the above gel, and the mixture was shaken at room temperature for 30 minutes. Then, 350 mg of $NaCNBH_3$ was added and the mixture was shaken for 8 hours, then filtered, and washed with 500 ml of 0.2M Tris-HCl buffer (pH 7.0) and, after filtration, further washed with 100 ml of 0.2M Tris-HCl buffer (pH 7.0) and then 0.055M citrate buffer (pH 7.0) to give an immobilized heparin. This product was designated as gel C.

EXAMPLE 2

Preparation of crosslinked polysaccharide sulfates

Each of the following gels was washed with physiological saline to give the object gel.

(1) Crosslinked cellulose sulfate ... Sulfated Cellulofine-c (Chisso, particle size 105–210 μm) (designated as gel D)

(2) Crosslinked cellulose sulfate ... Sulfated Cellulofine-m (Chisso, particle size 44–105 μm) (designated as gel E).

(3) Crosslinked chitin sulfate ... Sulfonated Chitopearl (Fuji Spinning) (designated as gel F)

EXAMPLE 3

FN adsorption test

Using the gels obtained in Examples 1 and 2, a plasma FN separation test was carried out as follows. First, the cFN concentration of commercial fresh frozen plasma samples (hereinafter referred to as FFP) was determined and samples showing high values not less than 10-fold as high as the normal value were pooled and designated as pool FFP. Then, 25 ml of this pool FFP was added to 1 ml of each gel and the mixture was gently shaken at room temperature. The supernatant was serially sampled and the amounts of plasma components were determined.

Concurrently, the pool FFP was subjected to the above procedure without addition of a gel and the amounts of plasma components were serially determined. Using the values thus found as references (100%), the amounts of respective components in each supernatant were expressed in percentage (%).

It was found that the cFN concentration of supernatants became substantially steady after 15 to 30 minutes and then continued to fall gradually and that the higher the degree of early concentration fall, the greater was the subsequent declining tendency. The results at 3 hours after commencement of the experiment are presented in Table 1.

TABLE 1

| Gel used | Concentration in supernatant (%) | | | |
|---|---|---|---|---|
| | cFN | Total FN | Albumin | Total protein |
| Gel A | 24.5 | 89.4 | 95.5 | 95.8 |
| Gel B | 39.0 | 98.3 | 100 | 100 |
| Gel D | 63.0 | 100 | 100 | 100 |
| Gel E | 56.1 | 100 | 100 | 100 |
| Gel F | 80.0 | 90.0 | 87.5 | 87.5 |

Based on the above data in Table 1, the adsorption rates (100-concentration in supernatant) (%) of each gel for various components were calculated. It was found that all the test gels adsorb cFN in preference to other protein components (high selectivity of cFN adsorption), indicating that these gels are useful cFN adsorbents.

EXAMPLE 4

Preparation of heparin-immobilized crosslinked cellulose

In the same manner as Example 1-(1) and (2), the reducing end (aldehyde) groups of heparin were coupled to crosslinked cellulose to give heparin-immobilized crosslinked celluloses with bound heparin contents of 3 mg/ml gel and 2 mg/ml gel. These immobilized heparin adsorbents were designated as gel a and gel b, respectively. The indicated amounts of bound heparin were measured in terms of the concentration of sulfur in each gel by the Oxygen Flask Combustion Method of the Japanese Pharmacopoeia XI and the same applies also to the examples that follows.

EXAMPLE 5

Preparation of heparin-immobilized crosslinked cellulose

In the same manner as Example 1-(3), the amino groups of heparin were coupled to crosslinked cellulose to give a heparin-immobilized crosslinked cellulose with a bound heparin content of about 2 mg/ml gel. This preparation was designated as gel c.

EXAMPLE 6

Preparation of heparin-immobilized crosslinked cellulose

In 80 ml of distilled water was dissolved a varying amount, from 0.12 to 2 g, of heparin and the solution was adjusted to pH 4.5 with 1M hydrochloric acid. Then, 50 ml of Amino-Cellulofine gel and 3 g of N-ethyl-N'-(3-dimethylaminopropyl)carbodiimide hydrochloride were added and the mixture was stirred at 4° C. overnight to give heparin-immobilized crosslinked celluloses wherein the carboxyl groups of heparin were coupled to crosslinked cellulose. The amounts of bound heparin in these adsorbents were 7 mg/ml gel and 3 mg/ml gel. These adsorbents are designated as gel g and gel h.

EXAMPLE 7

Preparation of crosslinked cellulose sulfate

In the same manner as Example 2-(1) and (2), sulfated Cellulofine-c (particle size 105–210 μm, sulfuric ester densities 10 and 20 μM/ml gel; designated as gel d and gel d') and sulfated Cellulofine-m (particle size 44–105 μm/ml gel; designated as gel e) were prepared.

EXAMPLE 8

Preparation of heparin-immobilized crosslinked agarose

To 4 g of CNBr-activated Sepharose B (Pharmacia), which is a crosslinked agarose activated with CNBr, was added 50 ml of 1 mM hydrochloric acid and the mixture was allowed to swell for 30 minutes. The resulting gel was subjected to a wash using 200 ml of 1 mM hydrochloric acid for a total of 4 times and further washed with 50 ml of a buffer solution [0.1M NaHCO₃-solution containing 0.5M NaCl (pH 8.3)]. Then, a solution of 0.2 g of heparin in 10 ml of the same buffer solution was added and the mixture was stirred at 4° C. overnight and filtered. The filtrate was removed and the gel was washed with 50 ml of 0.1M Tris-HCl buffer (pH 8.0) twice. The washed gel was put in 25 ml of 0.1M Tris-HCl buffer (pH 8.0) and the mixture was stirred at 4° C. for 2 hours. The above gel was then washed with 100 ml of 0.1M Tris-HCl buffer containing 0.5M of NaCl (pH 8.0) and 100 ml of 0.1M acetate buffer containing 0.5M of NaCl (pH 4.0) alternately for a total of 5 times each to give a heparin-immobilized crosslinked agarose (the amount of coupled heparin, about 2 mg/ml gel). This adsorbent was designated as gel i.

EXAMPLE 9

Preparation of dextran sulfate-immobilized crosslinked cellulose

To 10 ml of Cellulofine A-3 (Chisso), a cross-linked cellulose, were added 4 g of 20% NaOH, 12 g of heptane and one drop of Tween 20 and the mixture was stirred at 40° C. for 2 hours. Then, 5 g of epichlorohydrin was added and the mixture was further stirred for 2 hours. The reaction mixture was allowed to stand and the supernatant was discarded. The gel was washed with water to give an epoxy-activated cellulose gel. To 2 ml of this gel was added a solution of 0.5 g of sodium dextran sulfate (intrinsic viscosity 0.027 dl/g, average degree of polymerization 12, sulfur content 17.7 wt. %) in 2 ml of water and after its pH was adjusted to 12, the mixture was stirred at 40° C. for 16 hours. The gel was then recovered by filtration and washed successively with 2M NaCl, 0.5M NaCl and water to give a dextran sulfate-immobilized crosslinked cellulose. This adsorbent was designated as gel j.

EXAMPLE 10

FN adsorption test

Using each of the gels obtained in Examples 4 through 9 and the citrated plasma prepared as described below, an FN adsorption test was performed as in Example 3. However, the test temperature was 30° C. and the adsorption time was 4 hours. The citrated plasma was prepared by adding the cFN obtained from a culture supernatant of the cell line WI-38VA13, which was established by infecting the human normal fibroblast cell line WI-38 with a tumor virus, to citrated human plasma and its cFN concentration had been controlled at about 8 μg/ml.

As comparative examples, the crosslinked cellulose and crosslinked agarose were also subjected to the same test.

The test results (the concentrations of various components in each supernatant as determined in the same manner as Example 3) are presented below in Table 2.

TABLE 2

| Gel used | Concentrations in supernatant (%) | | | |
|---|---|---|---|---|
| | cFN | Total FN | Albumin | Total protein |
| Gel a | 31 | 92 | 96 | 95 |
| Gel b | 48 | 90 | 96 | 94 |
| Gel c | 7 | 44 | 96 | 94 |
| Gel g | 23 | 83 | 97 | 95 |
| Gel h | 30 | 87 | 95 | 94 |
| Gel d | 59 | 99 | 96 | 97 |
| Gel d' | 45 | 93 | 97 | 97 |
| Gel e | 61 | 98 | 97 | 97 |
| Gel i | 26 | 58 | 96 | 94 |
| Gel j | 37 | 85 | 96 | 95 |
| Crosslinked cellulose | 96 | 95 | 96 | 95 |
| Crosslinked agarose | 100 | 100 | 96 | 95 |

Based on the data in Table 2, the adsorption rates of each gel for the respective components were calculated as in Example 3. The results indicated that whereas the crosslinked cellulose and crosslinked agarose substantially did not absorb any protein, the adsorbents of the present invention selectively adsorbed FN and, in particular, cFN without appreciable adsorption of albumin and other proteins. Referring to the heparin-immobilized crosslinked cellulose, among the adsorbents of the invention, comparison of gel a with gel b or gel g with gel h reveals that the larger the amount of coupled heparin, the larger is the amount of cFN adsorbed. It is also clear that just like the above heparin-immobilized crosslinked cellulose, other immobilized polysaccharide sulfates also are useful selective adsorbents for cFN. As to crosslinked cellulose sulfate, comparison of gels d, d' and e indicates that the higher the sulfuric ester density, the higher is the adsorption selectivity for cFN.

EXAMPLE 11

Fractional purification of FN

The gel B which had adsorbed cFN in Example 3 was centrifuged, washed with 10 ml of 0.1M Tris-HCl buffer (pH 7.2) and packed into a column. Then, the above buffer was passed through the column at a flow rate of 1 ml/minute to wash the column until the effluent showed no UV absorption at 284 nm. Thereafter, stepwise gradient elution was carried out with 0.154-1M NaCl. The eluate was collected in 2.5 ml fractions and the total FN and cFN concentrations of each fraction were determined.

Figure 1:
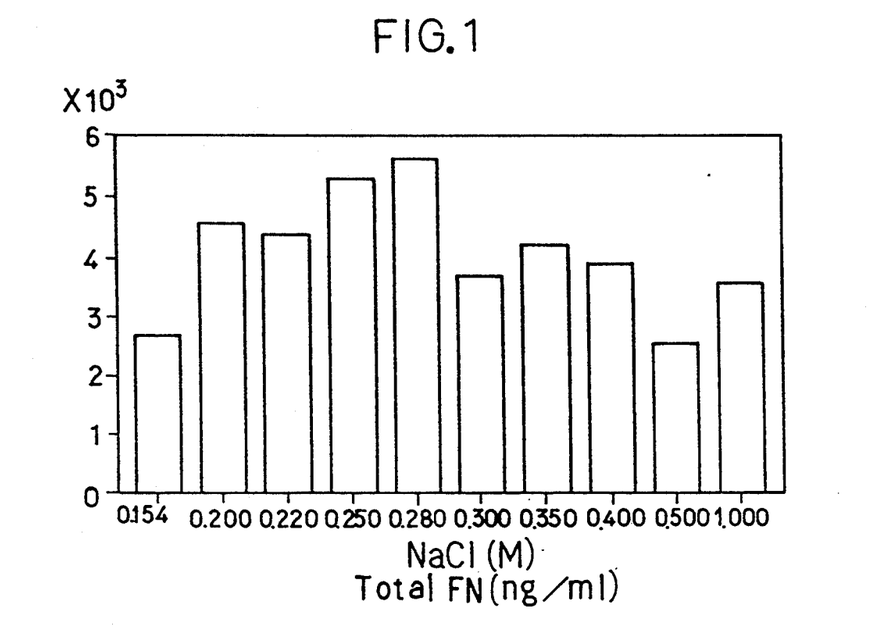
FIG. 1 is a graph showing the total FN concentrations of the fractions obtained by the FN fractional purification procedure described in Example 11.
Figure 2:
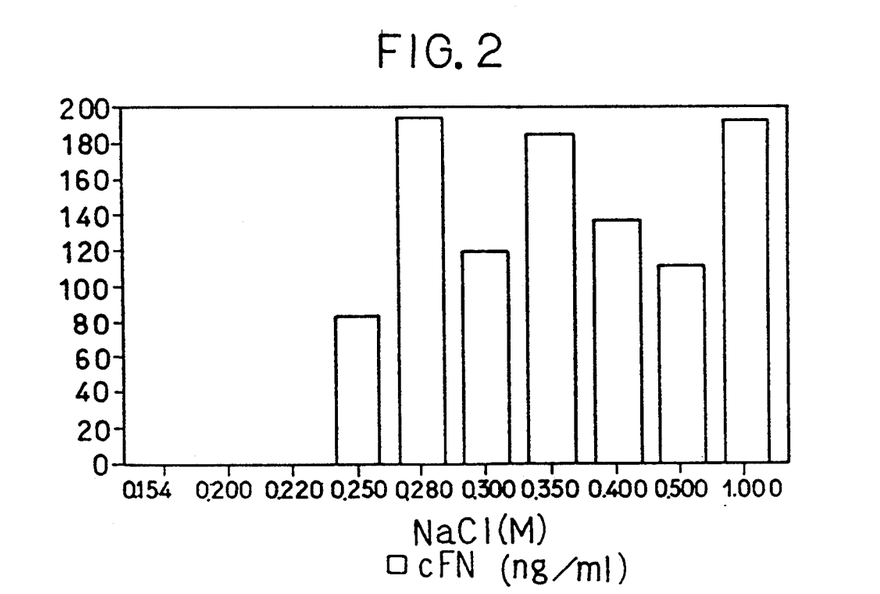
FIG. 2 is a graph showing the cFN concentrations of the fractions obtained by the FN fractional purification procedure described in Example 11.

The results are presented in FIG. 1 (total FN concentration, ng/ml) and FIG. 2 (cFN concentration, ng/ml).

Referring to FIGS. 1 and 2, total FN was eluted in all the fractions but cFN was not eluted at all in the fractions corresponding to the NaCl concentration range of 0.154 to 0.220M and emerged at higher NaCl concentrations.

The above results indicate that pure pFN, free of cFN, can be recovered by controlling the NaCl concentration or ion concentration of the eluent and that an FN solution rich in cFN can be recovered.

EXAMPLE 12

Fractional purification of pFN

To 1 ml of the gel g obtained in Example 6 was added 10 volumes of normal human plasma and the mixture was stirred at 30° C. for 4 hours. This gel was packed into a column and the plasma was allowed to flow down the column. The resulting effluent was recovered as a first fraction. The gel was then washed with 20 mM phosphate buffer (pH 7.0) until the effluent showed no UV absorption at 284 nm. Thereafter, elution was carried out with 20 mM phosphate buffer containing 0.15M of NaCl (pH 7.0) to recover a second fraction containing pFN.

For each of the above plasma and fractions, cFN and total FN concentrations were determined and the purity of pFN was calculated from the difference. The results are presented in Table 3.

TABLE 3

| | | pFN (ng/ml) | Total FN (ng/ml) | Purity of pFN (%) |
|---|---|---|---|---|
| Plasma | (10 ml) | 452.6 × 10³ | 454 × 10³ | 99.7 |
| First fraction | (10 ml) | 296.8 × 10³ | 297 × 10³ | 99.9 |
| Second fraction | (5 ml) | 55 × 10³ | 55 × 10³ | 100.0 |

It is clear from Table 3 that pFN, free of cFN, can be obtained by this method.

EXAMPLE 13

Fractional purification of cFN

To 4 ml of the gel g obtained in Example 6 was added 45 volumes of a plasma containing 7.2 μg/ml of cFN and the mixture was stirred at 30° C. for 4 hours. The gel was then packed into a column and the plasma was allowed to flow down the column. The gel was then washed with 20 mM phosphate buffer containing 0.15M NaCl (pH 7.0) until the effluent showed no UV absorption at 284 nm and elution was carried out with 20 mM phosphate buffer containing 1M of NaCl (pH 7.0) to recover cFN. The eluate was dialyzed against 20 mM phosphate buffer containing 0.15M of NaCl (pH 7.0) at 4° C. to obtain a first fraction.

To 5 volumes of the above first fraction was added 1 volume of gel g and the mixture was stirred at 30° C. for 4 hours. Then, the same procedure as above was repeated to obtain a second fraction.

For each of the above plasma and fractions, cFN and total FN concentrations were determined. The results are presented in Table 4.

TABLE 4

| | cFN (ng/ml) | Total FN (ng/ml) | Purity of cFN (%) |
|---|---|---|---|
| Plasma (180 ml) | 7.2 × 10³ | 401 × 10³ | 1.8 |
| First fraction | 31.1 × 10³ | 62 × 10³ | 50.2 |
| Second fraction | 29.9 × 10³ | 39 × 10³ | 76.7 |

It is clear from Table 4 that cFN can be highly concentrated by this method.

EXAMPLE 14

Temperature dependence test of immobilized heparin for cFN adsorption

To one volume of each of the gel a and gel g obtained in Examples 4 and 6 was added 25 volumes of plasma containing 8 μg/ml of cFN and the mixture was gently stirred at a various temperature for 4 hours. Then, cFN and total FN concentrations in each supernatant were determined as in Example 3. The results are presented in Table 5.

TABLE 5

| Adsorbent used | Concentration in supernatant (%) Gel a | | | |
|---|---|---|---|---|
| Test temperature | cFN (%) | Total FN (%) | Albumin (%) | Total protein (%) |
| 4° C. | 57 | 59 | 93 | 94 |
| 13° C. | 30 | 78 | 96 | 96 |
| 22° C. | 31 | 89 | 95 | 96 |
| 30° C. | 28 | 95 | 95 | 96 |
| 37° C. | 37 | 89 | 95 | 96 |
| Adsorbent used | Concentration in supernatant (%) Gel g | | | |
| Test temperature | cFN (%) | Total FN (%) | Albumin (%) | Total protein (%) |
| 4° C. | 46 | 42 | 96 | 95 |
| 13° C. | 19 | 83 | 95 | 97 |
| 22° C. | 20 | 87 | 95 | 95 |
| 30° C. | 20 | 80 | 96 | 95 |
| 37° C. | 24 | 82 | 96 | 95 |

Based on the data in Table 5, the adsorption rates of gels a and g for various plasma components were determined as in Example 3. Both the immobilized heparins (gels a and g) according to the invention showed the maximum cFN adsorption rates at 13° to 30° C., with decreases in the adsorption rate being observed outside the above range, particularly at 4° C., where a tendency of decreasing selectivity for cFN was observed.

APPLICATION EXAMPLE 1

Blood cleansing method

Figure 3:
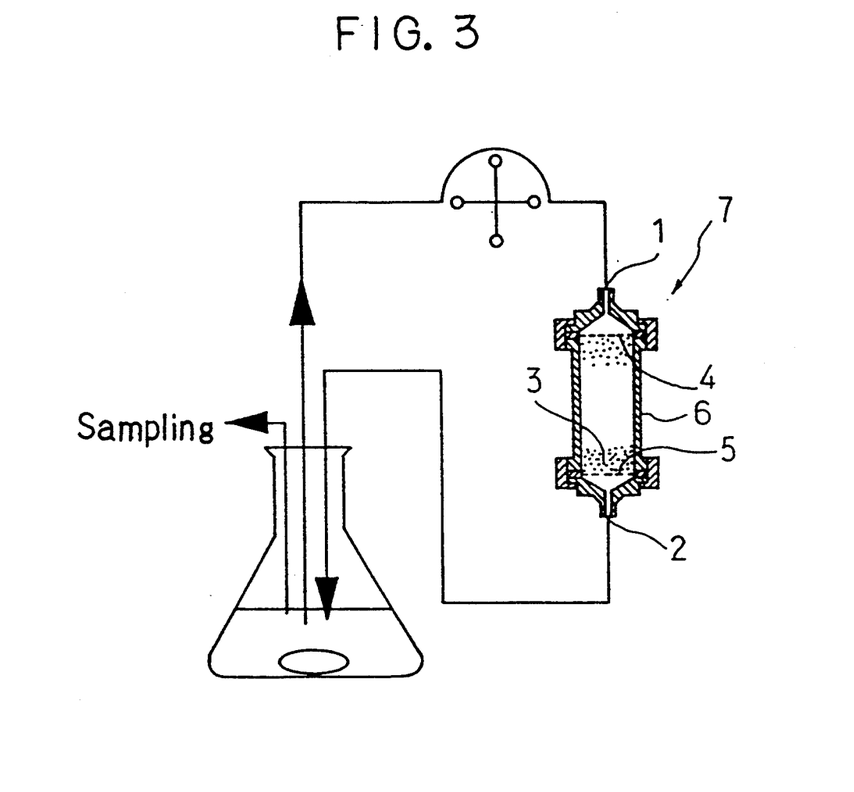
FIG. 3 is a schematic view showing the module, used as a plasma component separator, of the extracorporeal circulation system employed for blood cleansing as an application example of the method of the invention.

The plasma circuit illustrated in FIG. 3 was filled with 300 ml of plasma containing 3 U/ml of heparin, 10 mM of $CaCl_2$ and 8 μg/ml of cFN as purified from a culture medium of WI-38VA13 cells.

As the plasma component adsorption unit, a module (7) prepared by packing a column (16 mm dia. × 100 mm long) with 20 ml of gel g was used.

Referring to the module (7) shown in FIG. 3, the reference numeral (1) indicates a flow inlet, (2) a flow outlet, (3) an adsorbent (gel), (4) and (5) each a filter, and (6) a column.

The whole circuit was maintained at 30° C. and the plasma was circulated at a flow rate of 3 ml/minute for 150 minutes. The plasma was serially sampled and the protein concentrations of each sample were determined. The relative concentrations of plasma proteins at various time-points as calculated with the concentration of each protein immediately after the beginning of circulation being taken as 100% are presented below in Table 6.

TABLE 6

| Cerculatory time (min.) | Amount of plasma passed (ml) | Relative plasma protein concentration (%) | | | |
|---|---|---|---|---|---|
| | | cFN | Total FN | Albumin | Total protein |
| 30 | 90 | 74 | 80 | 96 | 95 |
| 60 | 180 | 59 | 80 | 96 | 95 |
| 90 | 270 | 44 | 78 | 95 | 95 |
| 120 | 360 | 39 | 79 | 96 | 95 |
| 150 | 450 | 29 | 82 | 95 | 95 |

It is apparent from Table 6 that the concentration of plasma proteins other than cFN were decreased by nonspecific adsorption only during the initial 30-minute period but changed little thereafter so that the total FN concentration was still about 80% and the concentrations of albumin and total protein not less than 95%. In contrast, the concentration of cFN was already as low as 74% at 30 minutes and continued to decline thereafter to ultimately fall under 30%. The above results indicate that the module (plasma component adsorption unit) embodying the method of the invention is capable of selective adsorption and removal of cFN from plasma.

It is, therefore, evident that by applying the present invention to extracorporeal circulation can cFN be selectively eliminated from blood clinically.

We claim:

1. A method for fractional purification of fibronectin characterized by contacting a fibronectin material containing plasma fibronectin and cellular fibronectin with a cellular fibronectin adsorbent comprising a crosslinked polysaccharide sulfate and/or an immobilized polysaccharide sulfate to fractionate plasma fibronectin and cellular fibronectin.

2. A method according to claim 1 wherein said crosslinked polysaccharide sulfate is selected from the group consisting of crosslinked cellulose sulfate, crosslinked agarose sulfate, crosslinked dextran sulfate, crosslinked chitin sulfate and crosslinked chitosan sulfate.

3. A method according to claim 1 wherein said crosslinked polysaccharide sulfate is selected from the group consisting of crosslinked cellulose sulfate and crosslinked chitin sulfate.

4. A method according to claim 1 wherein said immobilized polysaccharide sulfate is selected from the group consisting of immobilized heparin, immobilized dextran sulfate and immobilized cellulose sulfate.

5. A method according to claim 1 wherein said immobilized polysaccharide sulfate is selected from the group consisting of heparin-immobilized crosslinked cellulose, heparin-immobilized crosslinked agarose, heparin-immobilized crosslinked dextran, heparin-immobilized crosslinked chitin, heparin-immobilized crosslinked chitosan, dextran sulfate-immobilized crosslinked cellulose, dextran sulfate-immobilized crosslinked agarose, dextran sulfate-immobilized crosslinked dextran, dextran sulfate-immobilized crosslinked chitin, dextran sulfate-immobilized crosslinked chitosan, cellulose sulfate-immobilized crosslinked cellulose, cellulose sulfate-immobilized crosslinked agarose, cellulose sulfate-immobilized crosslinked dextran, cellulose sulfate-immobilized crosslinked chitin, cellulose sulfate-immobilized crosslinked chitosan, heparin-immobilized crosslinked polyvinyl alcohol and cellulose sulfate-immobilized crosslinked polyvinyl alcohol.

6. A method according to claim 1 wherein said immobilized polysaccharide sulfate is selected from the group consisting of heparin-immobilized crosslinked cellulose and dextran sulfate-immobilized crosslinked cellulose.

7. A method according to claim 1 wherein plasma fibronectin and cellular fibronectin are fractionated using an immobilized heparin for cellular fibronectin at a temperature in the range of 10° to 40° C.

* * * * *